(12) United States Patent
Auh et al.

(10) Patent No.: US 8,425,953 B2
(45) Date of Patent: Apr. 23, 2013

(54) **EXTRACT OF *COPTIDIS RHIZOMA* AND NOVEL USE THEREOF IN TREATING RESPIRATORY DISEASE**

(75) Inventors: Jin Auh, Seoul (KR); Chang-Hwan Kim, Hwaseong-si (KR); Chang-Kyun Han, Seoul (KR); Sung-Hum Yeon, Suwon-si (KR); Young-June Shin, Gimhae-si (KR); Min-Ki Shin, Seongnam-si (KR); Soo-Im Chang, Suwon-si (KR)

(73) Assignee: Ahn-Gook Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 12/996,646

(22) PCT Filed: Jun. 12, 2009

(86) PCT No.: PCT/KR2009/003170
§ 371 (c)(1),
(2), (4) Date: Dec. 7, 2010

(87) PCT Pub. No.: WO2009/151300
PCT Pub. Date: Dec. 17, 2009

(65) Prior Publication Data
US 2011/0081434 A1    Apr. 7, 2011

(30) Foreign Application Priority Data

Jun. 13, 2008    (KR) .................. 10-2008-0055537
Jun. 13, 2008    (KR) .................. 10-2008-0055538
Apr. 10, 2009    (KR) .................. 10-2009-0031344

(51) Int. Cl.
*A61K 36/00*    (2006.01)

(52) U.S. Cl.
USPC ........................................ 424/773; 424/725

(58) Field of Classification Search ................. None
See application file for complete search history.

(56) References Cited

U.S. PATENT DOCUMENTS

2006/0210660 A1    9/2006   Runkel et al.
2008/0317879 A1*  12/2008   Jung et al. ................ 424/725

FOREIGN PATENT DOCUMENTS

| CN | 1063042 | 7/1992 |
|---|---|---|
| CN | 1071076 | 4/1993 |
| CN | 1097139 A * | 1/1995 |
| CN | 09-095452 | 4/1997 |
| CN | 1175408 | 3/1998 |
| CN | 1418617 | 5/2003 |
| CN | 1425441 | 6/2003 |
| CN | 1682896 | 10/2005 |
| CN | 101045143 | 10/2007 |
| CN | 101085223 | 12/2007 |
| CN | 101091771 | 12/2007 |
| CN | 101091774 | 12/2007 |
| CN | 101181553 | 5/2008 |
| EP | 1374881 | 11/2001 |
| EP | 1374881 | 1/2004 |
| JP | 2006-522051 | 10/2004 |
| JP | 2007-505848 | 4/2005 |
| KR | 10-2004-0005070 | 1/2004 |
| WO | 2004087183 | 10/2004 |
| WO | 2005037298 | 4/2005 |
| WO | 2006025690 | 3/2006 |

OTHER PUBLICATIONS

Gulcin et al. (2004) Planta Med 70; pp. 561-563.*
Hofmann et al. (2003) Phytomedicine 10: pp. 213-220.*
Hecker M et al., Forsch Komplementarmed Klass Naturheilkd, 9(2), Apr. 2002, pp. 77-84.
Young-Chel Suh et al., Korean Journal of Oriental Medicine, 1996, 2, pp. 236-254.
Hofmann D et al., "Efficacy of dry extract of ivy leaves in children with bronchial asthma—a review of randomized controlled trails", Phytomedicine. Mar. 2003 vol. 10, p. 213-20.
China Patent and Trademark Office, office action for Chinese application No. 200980122243, Dec. 31, 2011.
European Patent Office, EESR for PCT/KR2009003170, Mar. 12, 2012.
Lee, Choong Jae et al. Effects of Baicalein, Berberine, Curcumin and Hesperidin on Mucin Release from Airway Goblet Cells, Planta med., vol. 69, No. 6, pp. 523-526, (Jun. 2003).

* cited by examiner

*Primary Examiner* — Chris R Tate
*Assistant Examiner* — Russell Fiebig
(74) *Attorney, Agent, or Firm* — Lexyoume IP Meister, PLLLC.

(57) ABSTRACT

A composition for suppressing cough, removing sputum, preventing and/or treating a respiratory disease comprising an extract of *Coptidis rhizoma* or a combined extract of *Coptidis rhizoma* with ivy leaf as an active ingredient, and a method of suppressing cough, removing sputum, and/or preventing and/or treating respiratory disease using the composition, are provided.

3 Claims, 3 Drawing Sheets

EXTRACT OF *COPTIDIS RHIZOMA* AND NOVEL USE THEREOF IN TREATING RESPIRATORY DISEASE

FIELD OF THE INVENTION

An extract of *Coptidis rhizoma* or a combined extract of *Coptidis rhizoma* with ivy leaf that is useful in expectorant, antitussive and/or antihistamine activities is provided. In particular, an antitussive and/or expectorant composition and/or a composition for preventing and treating respiratory diseases comprising the extract of *Coptidis rhizoma* or the combined extract of *Coptidis rhizoma* with ivy leaf as an active ingredient, and a method of preparing the same.

BACKGROUND OF THE INVENTION

Cough and sputum are known to be caused by physical or chemical factors, such as cold air, foreign substances including pathological microorganisms, air pollutants, allergen and the like, and can be divided according to the causes as follow:

First, if cough receptors, in the arynx, trachea, bronchus, pharynx, paranasal sinuses, diaphragm and the like, are stimulated by physicochemical factors, the stimulation is delivered to cough center in the medulla of the brain, whereby coughing reflex occurs.

Second, if parasympathetic nervous system is activated by physical or chemical factors, a smooth muscle of the bronchus is constricted, whereby symptoms such as bronchial convulsion and bronchoconstriction may occur.

Third, inflammatory mediators and the like are released from mast cells by physical or chemical factors.

Therefore, removal of the above factors can suppress cough and sputum. However, most of drugs developed so far are mainly synthetic chemicals and thus, cause various side effects. Natural drugs developed for compensating such defects cannot exhibit excellent effect to suppress cough and sputum.

Meanwhile, asthma, which is a representative respiratory disease, repeatedly and spasmodically shows symptoms such as difficult breathing, cough, stridulous breathing, and the like. Asthma may be divided into cardiac asthma and bronchial asthma. Although incidence rate of asthma is varied according to a country, a human race, age, and the like, it was reported in England at 2007 that about 7.9% of adults, 13.7% of children and 9.4% of older adults are suffered from asthma. In Korea, the incidence has been increased due to change in life style, environmental pollution, increase in stress, and the like. Recently, the severity of asthma has been maximized, since environmental pollution becomes serious, the age of incidence of asthma becomes lowered and the symptoms are more long lasted.

The respiratory obstruction, which is characteristic to asthma, occurs by 3-steps. Specifically, a smooth muscle of bronchus is constricted, pulmonary mucosa becomes thickened, and sticky mucus pools in bronchus and bronchioles, thereby respiratory tract being obstructed. Among these steps, only the constriction of smooth muscle of bronchus can be easily recovered.

In the mechanism of occurrence of exogenous (allergenic) asthma, IgE is especially important, and IgG relates thereto in part. IgE releases mediators, such as, histamine, SRS-A, ECF-A, NCF, PAF, Kinin, PGs and the like, which activate mast cells to cause hypersensitivity reaction. Endogenic (non-allergenic) asthma, although its mechanism has not been clarified, appears to be mediated by autonomic nerve. Choline stimulation in endogenic patients causes isolation of a mediator such as histamine from a mast cell directly through end organs, increase in the secretion of goblet cells, expansion of pulmonary blood vessel, and constriction of trachea, bronchus and bronchioles, thereby increasing bronchial convulsion and secretion of mucus.

Fundamental treatment of asthma has not been developed yet, and various methods and drugs for preventing a spasm and complications are developed; however, they simply ameliorate symptoms and cannot fundamentally treat disease, and they may cause serious side effects.

In order to overcome such limits of the existing drugs, there is a demand for development of novel drugs capable of fundamentally treating the cause and effectively ameliorating symptoms of disease. However, various leucocytes, and cytokines and inflammatory mediators separated therefrom are involved in respiratory disease, and thus the effective treatment is difficult with a single-component compound. Therefore, natural extract having various ingredients and mechanisms can be an effective drug, and thus, there is a demand for development of a drug based on natural extract.

DETAILED DESCRIPTION OF THE INVENTION

Technical Problem

As the results of studies for developing antitussives or expectorants, the present inventors identified that the extract of *Coptidis rhizoma* or combined extract of *Coptidis rhizoma* with ivy leaf has excellent antitussive, expectorant and antihistamine activities, to complete the present invention.

One embodiment provides a novel use of the extract of *Coptidis rhizoma* or combined extract of *Coptidis rhizoma* with ivy leaf for sputum removal, cough suppression, and/or treatment and/or prevention of respiratory diseases.

Another embodiment provides antitussive or expectorant composition and/or a composition for preventing and/or treating respiratory diseases, comprising the extract of *Coptidis rhizoma* or combined extract of *Coptidis rhizoma* with ivy leaf as an active ingredient, and a method for the preparation thereof.

Still another embodiment provides a method for suppressing cough, removing sputum, and/or treating and/or preventing respiratory diseases, comprising the step of administrating a composition comprising the extract of *Coptidis rhizoma* or combined extract of *Coptidis rhizoma* with ivy leaf as an active ingredient to a patient in need of cough suppression, sputum removal, and/or treatment and/or prevention of respiratory disease.

Technical Solution

One embodiment relates to a novel use of the extract of *Coptidis rhizoma* or combined extract of *Coptidis rhizoma* with ivy leaf in removing sputum, suppressing cough, and/or treating and/or preventing respiratory diseases.

Another embodiment relates to an antitussive or expectorant composition and/or a composition for preventing and/or treating respiratory diseases, comprising the extract of *Coptidis rhizoma* or combined extract of *Coptidis rhizoma* with ivy leaf as an active ingredient.

*Coptidis Rhizoma* is a perennial herb belonging to Ranunculaceae family, and its rhizome part is mainly used. It is known to contain alkaloid berberine, palmatine, coptisine, berberastine, magnoflorine, and the like, as main pharmacological components.

However, the effect of *Coptidis Rhizoma* extract and a *Coptidis Rhizoma* containing composition on antitussive, expectorant and antihistamine activities has not been studied yet.

The present inventors found that the extract of *Coptidis Rhizoma* has antitussive, expectorant and antihistamine activities, and is effective on the treatment and/or prevention of respiratory disease, to complete the present invention.

Ivy belongs to Araliaceae family, and it means a plant belonging to the genus *Hedera* (*Hedera* spp.). For examples, it may include, but not limited to, *Hedera algeriensis, Hedera azorica, Hedera canariensis, Hedera colchica, Hedera helix, Hedera hibernica, Hedera maderensis, Hedera nepalensis, Hedera pastuchowii, Hedera rhombea*, and the like. The antitussive and expectorant effects of dried ivy leaf extract have been revealed; however, it has not been reported yet that when the ivy leaf extract is administered combined with other herbal extracts, a significant synergistic effect can be obtained without side effects.

The present inventors identified that the combination of *Coptidis Rhizoma* extract and ivy leaf extract remarkably increases antitussive effect, expectorant effect, antihistamine effect, effect to suppress bronchoconstriction, effect to suppress airway hypersensitiveness, effect to suppress bronchial occlusion in lung tissue, and effect to suppress inflammatory cell infiltration, compared to each extract alone. In addition, in the present invention, optimum mixture ratio of *Coptidis Rhizoma* extract and ivy leaf extract showing maximum synergistic effect for pharmacological activities is suggested.

In order to maximize synergistic effects for antitussive, expectorant, antihistamine, bronchoconstriction suppression, airway hyperresponsivenss suppression, bronchial occlusion suppression in lung tissue, and inflammatory cell infiltration suppression activities by mixing *Coptidis Rhizoma* extract with ivy leaf extract, the mixture ratio of ivy leaf extract and *Coptidis Rhizoma* extract is 0.1:1 to 10:1, based on the weight of solid content (the weight of ivy leaf extract: the weight of *Coptidis Rhizoma* extract), preferably 0.2:1 to 5:1, more preferably 1:1 to 4:1, much more preferably 1.5:1 to 3.5:1, most preferably 2.5:1 to 3.5:1. The term 'solid content' means those from which a solvent used for preparing the extract is removed.

The term 'extract' herein means a crude extract of *Coptidis Rhizoma* and/or ivy leaf and/or a specific solvent-soluble extract or fraction of the crude extract, and it may be in the form of a solution, concentration or powder. The term 'combined extract of *Coptidis Rhizoma* with ivy leaf' means both a mixture of ivy leaf extract and *Coptidis Rhizoma* extract respectively obtained by extracting ivy leaf and *Coptidis Rhizoma*, and an extract obtained by extracting a mixture of ivy leaf and *Coptidis Rhizoma*.

The *Coptidis Rhizoma* extract may be a crude extract obtained by extracting *Coptidis Rhizoma*, preferably the rhizome part thereof with one or more solvents selected from the group consisting of water and linear or branched alcohol having 1 to 4 carbons, or a solvent-soluble extract obtained by adding one or more solvents selected from the group consisting of an aqueous solution of linear or branched alcohol having 1 to 6 carbons, preferably propyl alcohol aqueous solution, isopropyl alcohol aqueous solution and water-saturated butyl alcohol to the crude extract.

The ivy leaf extract may be a crude extract obtained by extracting dried ivy leaf with one or more solvents selected from the group consisting of water and linear or branched alcohol having 1 to 4 carbons, or a solvent-soluble extract obtained by adding one or more solvents selected from the group consisting of an aqueous solution of linear or branched alcohol having 1 to 6 carbons, preferably propyl alcohol aqueous solution, isopropyl alcohol aqueous solution and water-saturated butyl alcohol to the crude extract. Ivy used for preparing the ivy leaf extract may be *Hedera* spp., and for example, it may be one or more selected from the group consisting of *Hedera algeriensis, Hedera azorica, Hedera canariensis, Hedera colchica, Hedera helix, Hedera hibernica, Hedera maderensis, Hedera nepalensis, Hedera pastuchowii, Hedera rhombea*, and the like, but not limited thereto.

In a preferable embodiment, the solvent used for preparing the crude extract of *Coptidis Rhizoma* or ivy leaf may be one or more selected from the group consisting of water, 10 to 70% (v/v), preferably 20 to 60% (v/v), more preferably 25 to 55% (v/v) of linear or branched alcohol having 1 to 4 carbons, preferably methanol aqueous solution and ethanol aqueous solution, and water-saturated butyl alcohol.

The solvent used for preparing the solvent-soluble extract of *Coptidis Rhizoma* or ivy leaf may be one or more selected from the group consisting of 10 to 70% (v/v), preferably 20 to 60% (v/v), more preferably 25 to 55% (v/v) of linear or branched alcohol having 1 to 6 carbons, preferably propyl alcohol aqueous solution and isopropyl alcohol aqueous solution, and water-saturated butyl alcohol.

The combined extract of *Coptidis Rhizoma* with ivy leaf can be a mixture of *Coptidis Rhizoma* extract and ivy leaf extract, or an extract of a mixture of *Coptidis Rhizoma* and ivy leaf. For example, the combined extract may be a crude extract obtained by mixing *Coptidis Rhizoma* and ivy leaf, and extracting the mixture with one or more solvents selected from the group consisting of water and linear or branched alcohol having 1 to 4 carbons, or a solvent-soluble extract obtained by adding one or more solvents selected from the group consisting of an aqueous solution of lower alcohol having 1 to 6 carbons, preferably propyl alcohol aqueous solution and isopropyl alcohol aqueous solution, and water-saturated butyl alcohol, to the crude extract.

Preferably, the solvent used for preparing the crude extract of *Coptidis Rhizoma* and ivy leaf may be water, 10 to 70% (v/v), preferably 20 to 60% (v/v), more preferably about 25 to 55% (v/v) of methanol aqueous solution or ethanol aqueous solution, or water-saturated butyl alcohol. The solvent used for preparing the solvent-soluble extract may be one or more selected from the group consisting of 10 to 70% (v/v), preferably 20 to 60% (v/v), more preferably about 25 to 55% (v/v) of an aqueous solution of lower alcohol having 1 to 6 carbons, preferably propyl alcohol aqueous solution and isopropyl alcohol aqueous solution, and water-saturated butyl alcohol.

The 'fraction' may be obtained by subjecting the solvent-soluble extract to a silica gel column chromatography with a mixed solvent of methylene chloride and methanol (30:1 to 7:1 (v/v)).

The *Coptidis Rhizoma* extract, solvent-soluble extract or fraction comprises berberine, palmatine, coptisine, columbamine, and jatrorrhizine, preferably berberine (0.5 to 47.0 parts by weight): palmatine (0.2 to 21.4 parts by weight): coptisine (0.1 to 18.0 parts by weight): columbamine (0.1 to 3.2 parts by weight): jatrorrhizine (0.1 to 2.6 parts by weight).

In another aspect, the present invention relates to a method of preparing a combined extract of *Coptidis Rhizoma* with ivy leaf having antitussive, expectorant, antihistamine, bronchoconstriction suppression, airway hypersensitiveness suppression, bronchial occlusion suppression in lung tissue, and inflammatory cell infiltration suppression activities.

The method comprises the step of extracting *Coptidis Rhizoma*, preferably the rhizome part thereof with one or more solvents selected from the group consisting of water and linear or branched alcohol having 1 to 4 carbons, for example, water, 10 to 70% (v/v), preferably 20 to 60% (v/v), more preferably, about 25 to 55% (v/v) of methanol aqueous solution or ethanol aqueous solution, or water-saturated butyl alcohol.

The method of preparing the combined extract of *Coptidis Rhizoma* with ivy leaf may comprise the steps of:

extracting dried ivy leaf with one or more solvents selected from the group consisting of water and linear or branched alcohol having 1 to 4 carbons, for example, water, 10 to 70% (v/v), preferably 20 to 60% (v/v), more preferably 25 to 55% (v/v) of methanol aqueous solution or ethanol aqueous solution, or water-saturated butyl alcohol, to obtain ivy leaf extract;

extracting *Coptidis Rhizoma*, preferably the rhizome part thereof with one or more solvents selected from the group consisting of water and linear or branched alcohol having 1 to 4 carbons, for example, water, 10 to 70% (v/v), preferably 20 to 60% (v/v), more preferably 25 to 55% (v/v) of methanol aqueous solution, or ethanol aqueous solution, or water-saturated butyl alcohol, to obtain *Coptidis Rhizoma* extract; and mixing the obtained ivy leaf extract and *Coptidis Rhizoma* extract at a ratio of 0.1:1 to 10:1 (the weight of ivy leaf extract: the weight of *Coptidis Rhizoma* extract), preferably 0.2:1 to 5:1, more preferably 1:1 to 4:1, much more preferably 1.5:1 to 3.5:1, most preferably 2.5:1 to 3.5:1, based on the solid content.

The step of preparing ivy leaf extract and the step of preparing *Coptidis Rhizoma* extract may further comprise the step of adding one or more solvents selected from the group consisting of linear or branched alcohol having 1 to 6 carbons, preferably water-saturated butyl alcohol, propyl alcohol and isopropyl alcohol to the obtained extract, to obtain a solvent-soluble extract.

The step of preparing the ivy leaf extract will be explained in detail: Ivy leaf is cut and washed with water to remove impurities, and the leaf is dried, and then, reflux-extracted with one or more solvents selected from the group consisting of water and linear or branched alcohol having 1 to 4 carbons, for example, water, 10 to 70% (v/v), preferably 20 to 60% (v/v), more preferably 25 to 55% of methanol aqueous solution or ethanol aqueous solution, or water-saturated butyl alcohol, in an amount of about 5 to 20 times by volume, preferably 7 to 15 times by volume of the dried ivy leaf. The extraction temperature is 40 to 110° C., preferably 55 to 90° C.

After extraction, the extract is filtered to collect filtrate, and the residue is reflux-extracted with one or more solvents selected from the group consisting of water and linear or branched alcohol having 1 to 4 carbons, for example, water, 10 to 70% (v/v), preferably 20 to 60% (v/v), more preferably 25 to 55% of methanol aqueous solution or ethanol aqueous solution, or water-saturated butyl alcohol, in an amount of about 5 to 15 times by volume, preferably 8 to 12 times by volume. Extraction temperature is, although not specifically limited, 40 to 110° C., preferably 55 to 90° C. After extraction, the extract is filtered, the filtrate is combined with previously obtained filtrate, and they are concentrated under the vacuum to prepare ivy leaf extract. The twice extractions and combination of the filtrates obtained after each extraction can increase extraction efficiency, but the number of extraction is not limited thereto.

The step of preparing *Coptidis rhizoma* extract will be explained in detail: The rhizome part of *Coptidis rhizoma* is chopped into small pieces, and then, one or more solvents selected from the group consisting of water and linear or branched alcohol having 1 to 4 carbons, for example, water, 10 to 70% (v/v), preferably 20 to 60% (v/v), more preferably 25 to 55% of methanol aqueous solution or ethanol aqueous solution, or water-saturated butyl alcohol, is added thereto in an amount of about 3 to 20 times by volume, preferably 5 to 15 times by volume of the raw material to extract for 0.5 to 20 hours, preferably 1 to 10 hours, more preferably 2 to 5 hours. The extraction temperature is, although not specifically limited, preferably 40 to 110° C., preferably 55 to 90° C. Preferably, the obtained extract is filtered to collect filtrate, and one or more solvents selected from the group consisting of water and linear or branched alcohol having 1 to 4 carbons, for example, water, 10 to 70% (v/v), preferably 20 to 60% (v/v), more preferably 25 to 55% of methanol aqueous solution or ethanol aqueous solution, or water-saturated butyl alcohol, is added to the reside in an amount of about 5 to 15 times by volume, preferably 8 to 12 times by volume, and temperature is elevated to re-extract for 1 to 10 hours, preferably 2 to 5 hours, and then, the extract is filtered and concentrated under the vacuum to obtain *Coptidis rhizoma* extract. Combination of the obtained extract with previously obtained filtrate can increase extraction efficiency.

The twice extractions and combination of the filtrates obtained after each extraction may increase extraction efficiency, but the number of extraction is not limited thereto.

If the amount of the solvent used for preparing *Coptidis rhizoma* extract and/or ivy leaf extract is too small, stirring is difficult and solubility of the extract decreases to lower extraction efficiency. If the amount of the solvent used for preparing *Coptidis rhizoma* extract and/or ivy leaf extract is too much, the amount of lower alcohol used for next purification step becomes increased to cause economical problems and problems in handling. Thus, it is preferable to adjust the amount of the solvent within the above described range.

According to one preferred embodiment of the present invention, re-extraction may be made after primary extraction, which is to prevent decrease in extraction efficiency by performing primary extraction only, because in case herb extract is produced in large quantity, even if effective filtration is made, the amount of extract of herb is high, thereby generating losses thereof, and thus, the extraction efficiency becomes decreased when only primary extraction is performed. Therefore, according to one preferred embodiment of the present invention, re-extraction may be made after primary extraction. In addition, as result of examining extraction efficiency in each step, it has been found that about 80 to 90% of total extract amount is extracted by secondary extraction, and thus, it may be suggested that two-step extractions allows significant economical efficacy compared to multistep extractions more than third extraction.

The solvent-soluble extract may be prepared by suspending the obtained crude extract in about 2 to 10 times, preferably about 3 to 7 times by volume of water, and adding thereto one or more solvents selected from the group consisting of an aqueous solution of linear or branched alcohol having 1 to 6 carbons, preferably aqueous solution of propyl alcohol or aqueous solution of isopropyl alcohol, and water-saturated butyl alcohol in an amount of 0.5 to 3 times, preferably equivalent amount to 2 times of the suspension for once to five times, preferably twice to three times, to extract a solvent-soluble layer, and then concentrating under the vacuum.

The step of solvent-soluble extraction using lower alcohol is to purify unnecessary impurities such as proteins, polysaccharides, fatty acids, and the like. If the amount of the lower alcohol used therefor is small compared to filtrate, fine particles form of unnecessary ingredients such as fatty acid, thereby making layer separation unsmooth and decreasing extraction amount of active ingredients. Therefore, it may be preferable to adjust the amount of the lower alcohol within the above described range.

The lower alcohol fraction obtained after layer separation is concentrated under the vacuum at 50 to 60° C. to remove remaining solvent in the sample.

In order to control the content of the remaining lower alcohol in the obtained concentrate so as to make it suitable for use as raw material for medicine, the concentrate may be subjected to azeotropic concentration with about 10 to 30 times, preferably 15 to 25 times, more preferably about 20 times by weight of water, based on the total amount of the concentrate, for 1 to 5 times, preferably 2 to 3 times, and equivalent amount of water is added thereto to homogenously suspend it, and then, the suspension is lyophilized to prepare *Coptidis Rhizoma* extract and/or ivy leaf extract in powder form.

Preferably, in order to homogenously combine each extract in the combined extract, about 2 to 3 times by weight of water is added to the combined extract, and then it is concentrated under the vacuum at 50 to 60° C., equivalent amount of water is added again to the concentrate to homogenously suspend it, and then the suspension is lyophilized to prepare a composition in powder form.

According to another embodiment, the method for preparing combined extract of *Coptidis Rhizoma* with ivy leaf may comprise the steps of:

mixing dried ivy leaf and *Coptidis Rhizoma*, preferably the rhizome part thereof at a weight ratio of 1:4 to 7:1 (the weight of ivy leaf: the weight of *Coptidis Rhizoma*), preferably 1:1 to 6:1, more preferably 2:1 to 5:1 to prepare a mixture of ivy leaf and *Coptidis Rhizoma*; and extracting the mixture with one or more solvents selected from the group consisting of water and linear or branched alcohol having 1 to 4 carbons, for example, water, 10 to 70% (v/v), preferably 20 to 60% (v/v), more preferably about 25 to 55% (v/v) of methanol aqueous solution or ethanol aqueous solution, or water-saturated butyl alcohol.

The above method may further comprise the step of adding one or more solvents selected from the group consisting of linear or branched lower alcohol having 1 to 6 carbons, preferably propyl alcohol, isopropyl alcohol and water-saturated butyl alcohol, to obtain solvent-soluble extract, after the step of obtaining extract of the mixture of ivy leaf and *Coptidis Rhizoma*.

The details of the steps of preparing the crude extract and the solvent-soluble extract are as described in the preparation of each herb extract As the extraction method used in the present invention, any conventionally used method may be used. For examples, the extraction may be performed through extraction at room temperature, hot water extraction, ultrasonic extraction, reflux extraction or cooling extraction, but not limited thereto.

In another aspect, the present invention provides an antitussive composition comprising the extract of *Coptidis Rhizoma* or a combined extract of *Coptidis Rhizoma* with ivy leaf as an active ingredient. In another aspect, the present invention also provides an expectorant composition comprising the extract of *Coptidis Rhizoma* or a combined extract of *Coptidis Rhizoma* with ivy leaf as an active ingredient. In still another aspect, the present invention also provides a composition for preventing and/or treating respiratory disease comprising the extract of *Coptidis Rhizoma* or a combined extract of *Coptidis Rhizoma* with ivy leaf as an active ingredient.

In another aspect, the present invention provides a method of suppressing cough comprising the step of administrating the extract of *Coptidis Rhizoma* or a combined extract of *Coptidis Rhizoma* with ivy leaf to a patient in a therapeutically effective amount. In another aspect, the present invention also provides a method of removing sputum comprising the step of administrating the extract of *Coptidis Rhizoma* or a combined extract of *Coptidis Rhizoma* with ivy leaf to a patient in a therapeutically effective amount. In still another aspect, the present invention also provides a method of preventing and/or treating respiratory disease comprising the step of administrating the extract of *Coptidis Rhizoma* or a combined extract of *Coptidis Rhizoma* with ivy leaf to a patient in a therapeutically effective amount. The patient may be any mammals in need of cough suppression, sputum removal or treatment and/or prevention of respiratory disease, preferably human.

The therapeutically effective amount is a determined dosage for obtaining desired treatment effect. It can be varied depending on age, weight, sex distinction, dosage form, health condition and severity of disease, and it can be also varied depending on the judgment of physician or pharmacist. For example, dosage per day may be 0.5 to 500 mg/kg, preferably 1 to 300 mg/kg, based on the content of active ingredient, but not limited thereto. The dosage can be administrated once a day or several times a day. The dosage illustrates for average case, and it can be higher or lower individually. If dosage per day of the composition comprising the combined extract of the present invention is less than the above described range, significant effect cannot be obtained; and if it exceeds the above described range, economical efficiency deceases and the dosage is out of common dosage thus causing undesirable side effect. Thus, the dosage per day is preferably in the above described range.

The extract of *Coptidis Rhizoma* and a combined extract of *Coptidis Rhizoma* with ivy leaf show antitussive, expectorant, antihistamine, bronchoconstriction suppression, airway hyperreactivity suppression, bronchial occlusion suppression in lung tissue, and inflammatory cell infiltration suppression activities, and thus they can be used for treating, preventing or alleviating related respiratory diseases. And, the combined extract of *Coptidis Rhizoma* with ivy leaf is preferable because synergism can be obtained compared to each extract alone.

The respiratory disease may be all the disease involving cough and sputum, and for examples, it is selected from the group consisting of common cough or sputum; pulmonary emphysema involving cough or sputum; bronchitis such as chronic bronchitis, acute bronchitis, catarrhal bronchitis, obstructive or inflammatory bronchial disease, etc.; asthma such as bronchial asthma, atopic asthma, atopic bronchial IgE-mediated asthma, non-atopic asthma, allergic asthma, non-allergic asthma, etc.; chronic or acute bronchoconstriction; stridulus infant syndrome; chronic obstructive pulmonary disease; bronchial adenoma; solitary pulmonary nodule; pulmonary tuberculosis; pyothorax; pulmonary abscess; common cold; influenza; and pulmonary histiocytosis.

The composition of the present invention can be administered to mammals including human in various routes. It can be administered using commonly used method, for examples, it can be administered orally, intrarectally, or by intravenous, intramuscular, subcutaneous, intrauterine or intracerebroventricular injection. The composition of the present invention can be formulated into an oral dosage form such as powder, granule, tablet, capsule, suspension, emulsion, syrup, aerosol, etc., or a parenteral dosage form such as transdermal agent, suppository and sterile injection solution, etc.

The composition of the present invention may further comprise pharmaceutically suitable and physiologically acceptable adjuvant such as carrier, excipient and diluents.

The composition of the present invention can be administered alone; however, in general, considering administration route and standard pharmaceutical practice, it can be administered with a selected pharmaceutical carrier. For example, the composition can be administered orally, intrabuccally or sublingually in the form of tablet containing lactose or starch, capsule alone or containing excipient, elixir containing flavoring or coloring chemicals, or suspension. The liquid formulation can be formulated with pharmaceutically acceptable additives such as suspension agent (for example, methylcellulose, semi-synthetic glyceride such as witepsol, or a glyceride mixture such as a mixture of apricot kernel oil and PEG-6 ester, or a mixture of PEG-8 and caprylic/capric glyceride)

In another aspect, the present invention provides a health functional food for suppressing cough, removing sputum, or preventing or ameliorating respiratory disease such as asthma, comprising the extract of *Coptidis Rhizoma* or a combined extract of *Coptidis Rhizoma* with ivy leaf. The health functional food can be food, beverage, or food additives, etc.

The content of the extract as an active ingredient contained in the health functional food can be appropriately varied depending on the form of food, desired use, etc., without specific limitations. For example, it can be added in an amount of 0.01 to 15 wt % of the total food, and for health beverage composition, it can be added in an amount of 0.02 to 10 g, preferably 0.3 to 1 g, based on 100 ml of the composition.

In case the herbal composition of the present invention is administered into human body, considering general properties of natural extracts, it is believed that there is no concern of side effects compared to other synthetic medicines, and as results of practical toxicity test, it is proven to have no influence on a living body.

EXAMPLES

Figure 1:
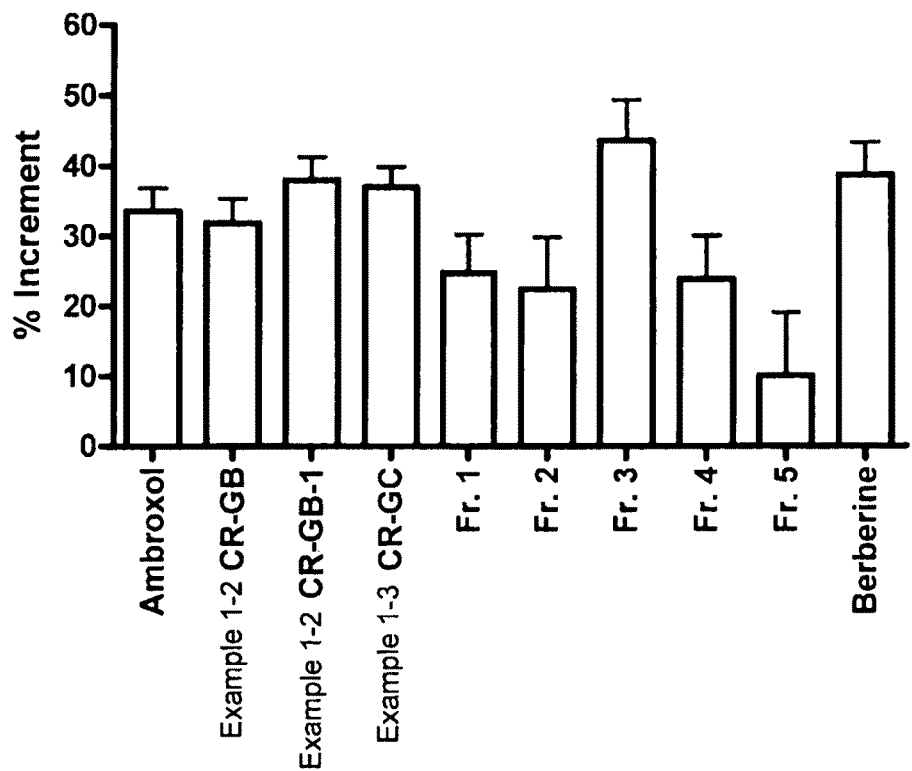
FIG. 1 shows expectorant activities of *Coptidis Rhizoma* extract and the active fraction and representative ingredients thereof through phenol red secretion method in a mouse model.

The present invention will be explained in detail with reference to the following examples and experiments.

However, the following examples and experiments are only to illustrate the present invention, and the scope of the present invention is not limited thereto.

Example 1

Preparation of the Extract of *Coptidis Rhizoma*

1-1. Preparation of the Extract of *Coptidis Rhizoma* Using Water 1-1-1. Preparation of Crude Extract of *Coptidis Rhizoma* (CR-GA)

*Coptidis Rhizoma* purchased from Kyungdong market was washed with water to remove impurities, and, 250 g of dried *Coptidis Rhizoma* was subjected to hot water extraction with 1.5 L of water at 80° C. twice each for 3 hours, and then, the extract was filtered and concentrated under the vacuum to obtain 62.5 g of crude extract (25% yield compared to raw herb), which was named as 'CR-GA', and used in the following Example 1-2.

1-1-2. Preparation of Solvent-Soluble Extract of *Coptidis Rhizoma* (CR-GA-1)

To 62.5 g of CR-GA obtained in the Example 1-1-1, 0.5 L of water was added to suspend it, and 1 L of water-saturated butyl alcohol was added thereto, to separate a layer twice, and then, only water-saturated butyl alcohol fraction was collected and concentrated under the vacuum until dried. When most of butyl alcohol and water was evaporated, 0.4 L of water was added to azeotropically concentrate it, which was repeated twice. And, finally, 0.1 L of distilled water was added to suspend the concentrate, and then, the suspension was lyophilized to obtain 19.8 g of *Coptidis Rhizoma* extract in powder form (7.92% yield compared to raw herb), which was named as 'CR-GA-1', and used as a sample in the following Experiments.

1-2. Preparation of the Extract of *Coptidis Rhizoma* Using 50% (v/v) Ethanol 1-2-1. Preparation of Crude Extract of *Coptidis Rhizoma* (CR-GB)

*Coptidis Rhizoma* purchased from Kyungdong market was washed with water to remove impurities, and, 250 g of dried *Coptidis Rhizoma* was extracted by reflux with 2.0 L of 50% (v/v) ethanol aqueous solution at 80° C. twice each for 3 hours, and then, the extract was filtered and concentrated under the vacuum to obtain 57.5 g of crude extract (23% yield compared to raw herb), which was named as 'CR-GB', and used in the following Example 2-2.

1-2-2. Preparation of Solvent-Soluble Extract of *Coptidis Rhizoma* (CR-GB-1)

To 57.5 g of CR-GB obtained in the Example 1-2-1, 0.3 L of water was added to suspend it, and 0.6 L of water-saturated butyl alcohol was added thereto, to separate a layer twice, and then, only butyl alcohol fraction was collected and concentrated under the vacuum until dried. When most of butyl alcohol and water was evaporated, 0.2 L of water was added to azeotropically concentrate it, which was repeated twice. And, finally, 0.2 L of distilled water was added to suspend the concentrate, and then, the suspension was lyophilized to obtain 31.8 g of *Coptidis Rhizoma* extract in powder form (12.7% yield compared to raw herb), which was named as 'CR-GB-1', and used as a sample in the following Experiments.

1-3. Preparation of the Extract of *Coptidis Rhizoma* Using Water-Saturated Butyl Alcohol 1-3-1. Preparation of the Extract of *Coptidis Rhizoma* (CR-GC)

*Coptidis Rhizoma* purchased from Kyungdong market was washed with water to remove impurities, and, 250 g of dried *Coptidis Rhizoma* was extracted by reflux with 2.5 L of water-saturated n-butyl alcohol at 85° C. twice each for 3 hours, and then, the extract was filtered and concentrated under the vacuum. When most of butyl alcohol was evaporated, 0.2 L of water was added to azeotropically concentrate it, which was repeated twice. Finally, 0.2 L of distilled water was added to suspend it, and the suspension was lyophilized to obtain 32.8 g of extract in powder form (13.1% yield compared to raw herb), which was named as 'CR-GC', and used in the following Experiments.

1-4. Separation of *Coptidis Rhizoma* Extract 20 g of CR-GB-1 obtained in the Example 1-2-2 was divided into 5 fractions by silica gel column chromatography using a mixed solvent of methylene chloride and methanol (30:1~7:1 (v/v). Fr. 1 was 0.8 g (hereinafter, referred to as 'Fr. 1'), Fr. 2 was 2.6 g (hereinafter, referred to as 'Fr. 2'), Fr. 3 was 5.5 g (hereinafter, referred to as 'Fr. 3'), Fr. 4 was 2.8 g (hereinafter, referred to as 'Fr. 4'), Fr. 5 was 6.5 g (hereinafter, referred to as 'Fr. 5'), which were used as samples in the following Experiments.

Example 2

Preparation of Combined Extract of *Coptidis Rhizoma* With Ivy Leaf

Preparation of Ivy Leaf Extract

Ivy (*Hedera helix*) leaves were washed with water to remove impurities and completely dried. To 250 g of the prepared ivy leaves, 3 l 30% (v/v) ethanol aqueous solution was added, and extracted by reflux for 6 hours, and then, the extract was filtered to collect filtrate. To the residue, 2.5 l of 30% (v/v) ethanol aqueous solution was added, extracted by reflux at 80° C. for 3 hours, and the obtained filtrated was combined with previously collected filtrated and it was concentrated the vacuum. When most of the solvent was evaporated, 0.2 l of water was added to azetropically concentrate it, which was repeated twice. And, equivalent amount of water was added to homogenously suspend it, and then, the suspension was lyophilized to obtain 42.4 g of ivy leaf extract in powder form. The obtained ivy leaf extract was used for the preparation of combined extract in the following Examples 2-1 to 2-11.

Preparation of the Extract of *Coptidis rhizoma*

*Coptidis rhizoma* was washed with water to remove impurities and completely dried. To 250 g of the prepared *Coptidis rhizoma*, 2.0 L of 50% (v/v) ethanol aqueous solution was added to reflux-extract at 80° C. for 3 hours. And, then, the extract was filtered and concentrated under the vacuum to obtain 57.5 g of crude extract. And, 0.3 L of water was added thereto to suspend it, and 0.6 L of water-saturated butyl alcohol was added thereto, to separate a layer twice. And then, only butyl alcohol fraction was collected and concentrated under the vacuum until dried. When most of butyl alcohol and water were evaporated, 0.2 l of water was added to azeotropically concentrate it, which was repeated twice. Finally, an equivalent amount of water was added thereto to suspend it, and the suspension was lyophilized to obtain 31.8 g of *Coptidis Rhizoma*, which was used for preparation of combined extract in the following Examples 2-1 to 2-11.

2-1. Preparation of Combined Extract (0.2:1)

The above prepared ivy leaf extract and *Coptidis Rhizoma* extract were mixed at a weight ratio of 0.2:1 (the weight of ivy leaf extract: the weight of *Coptidis Rhizoma* extract). In order to homogenously mix, about 2 to 3 times by weight of water was added to the combined extract, and then it was concentrated under the vacuum at a temperature of 50 to 60° C. And, an equivalent amount of water was added again to the obtained concentrate to homogenously suspend it, and the suspension was lyophilized to prepare a combined extract in powder form.

2-2. Preparation of Combined Extract (0.4:1)

A combined extract was prepared by the same method as the above Preparation Example 1, except that the ratio of the prepared ivy leaf extract and *Coptidis Rhizoma* extract was changed to 0.4:1 (the weight of ivy leaf extract: the weight of *Coptidis Rhizoma*)

2-3. Preparation of Combined Extract (1:1)

A combined extract was prepared by the same method as the above Preparation Example 1, except that the ratio of the prepared ivy leaf extract and *Coptidis Rhizoma* extract was changed to 1:1 (the weight of ivy leaf extract: the weight of *Coptidis Rhizoma*)

2-4. Preparation of Combined Extract (1.5:1)

A combined extract was prepared by the same method as the above Preparation Example 1, except that the ratio of the prepared ivy leaf extract and *Coptidis Rhizoma* extract was changed to 1.5:1 (the weight of ivy leaf extract: the weight of *Coptidis Rhizoma*)

2-5. Preparation of Combined Extract (2:1)

A combined extract was prepared by the same method as the above Preparation Example 1, except that the ratio of the prepared ivy leaf extract and *Coptidis Rhizoma* extract was changed to 2:1 (the weight of ivy leaf extract: the weight of *Coptidis Rhizoma*)

2-6. Preparation of Combined Extract (2.5:1)

A combined extract was prepared by the same method as the above Preparation Example 1, except that the ratio of the prepared ivy leaf extract and *Coptidis Rhizoma* extract was changed to 2.5:1 (the weight of ivy leaf extract: the weight of *Coptidis Rhizoma*).

2-7. Preparation of Combined Extract (3:1)

A combined extract was prepared by the same method as the above Preparation Example 1, except that the ratio of the prepared ivy leaf extract and *Coptidis Rhizoma* extract was changed to 3:1 (the weight of ivy leaf extract: the weight of *Coptidis Rhizoma*).

2-8. Preparation of Combined Extract (3.5:1)

A combined extract was prepared by the same method as the above Preparation Example 1, except that the ratio of the prepared ivy leaf extract and *Coptidis Rhizoma* extract was changed to 3.5:1 (the weight of ivy leaf extract: the weight of *Coptidis Rhizoma*)

2-9. Preparation of Combined Extract (4:1)

A combined extract was prepared by the same method as the above Preparation Example 1, except that the ratio of the prepared ivy leaf extract and *Coptidis Rhizoma* extract was changed to 4:1 (the weight of ivy leaf extract: the weight of *Coptidis Rhizoma*)

2-10. Preparation of Combined Extract (4.5:1)

A combined extract was prepared by the same method as the above Preparation Example 1, except that the ratio of the prepared ivy leaf extract and *Coptidis Rhizoma* extract was changed to 4.5:1 (the weight of ivy leaf extract: the weight of *Coptidis Rhizoma*)

2-11. Preparation of Combined Extract (5:1)

A combined extract was prepared by the same method as the above Preparation Example 1, except that the ratio of the prepared ivy leaf extract and *Coptidis Rhizoma* extract was changed to 5:1 (the weight of ivy leaf extract: the weight of *Coptidis Rhizoma*)

Example 3

Experiment for Activity of *Coptidis Rhizoma* Extract 3-1. Measurement of Expectorant Activity of *Coptidis Rhizoma* Extract

[Experiment Method]

In order to measure expectorant activities of *Coptidis Rhizoma* extracts of the Examples 1-1 to 1-3, experiment was conducted using Engler et al. method (Engler H, Szelenyi I, J.

Pharmacol. Moth. 11, 151~157, 1984,; Bao-quin Lin et., Pulmonary Pharmacology & Therapeutics 21, 259~263, 2008.) in the following procedure.

A positive control drug (ambroxol, Sigma) and test drugs (*Coptidis Rhizoma* extract of Examples 1-1 to 1-3) were orally administered to a male mouse (8-weeks age, Sam tako BioKorea), and after 30 minutes, 500 mg/kg of phenol red was intraperitoneally injected (phenol red was dissolved in saline). After 30 minutes, the mouse was anesthetized with diethyl ether, exsanguinated by cutting the abdominal aorta, and then the whole trachea was resected. The separated trachea was put in 1 ml of saline and washed for 30 minutes, centrifuged at 10,000 rpm at room temperature for 5 minutes, 1 N sodium hydroxide (NaOH) was added to supernatant (adding 0.1 ml of 1 N NaOH per 1 ml of supernatant), and then, absorbance was measured at 546 nm to measure expectorant activity as concentration of phenol red.

[Experiment Results]

The obtained results are presented in the following Table 1

TABLE 1

|  |  | dosage (mg/kg) | Capacity to secrete sputum (%) |
|---|---|---|---|
| Example 1-1 | CR-GA | 500 | 29 |
|  | CR-GA-1 | 500 | 36 |
| Example 1-2 | CR-GB | 500 | 32 |
|  | CR-GB-1 | 500 | 41 |
| Example 1-3 | CR-GC | 500 | 38 |
| Positive control (Ambroxol) |  | 250 | 32 |

As results of experiment, as shown in the above Table 1, the extracts had excellent activities as a whole, particularly CR-GB-1 of Example 2 showed most excellent sputum secretion activity.

And, activities of CR-GC-1 of Example 2 according to dosage (50, 100, 150, 200, 500 mg/kg) were measured, of which results are presented in the following Table 2.

TABLE 2

|  |  | Dosage (mg/kg) | Capacity to secrete sputum (%) |
|---|---|---|---|
| Example 1-2 | CR-GB-1 | 50 | 4 |
|  |  | 100 | 22 |
|  |  | 150 | 32 |
|  |  | 200 | 33 |
|  |  | 500 | 41 |
| Positive control (Ambroxol) |  | 250 | 30 |

As results of experiment, as shown in the above Table 2, CR-GB-1 of Example 1-2 showed most excellent sputum secretion activity at a dosage of 500 mg/kg.

3-2. Measurement of Antitussive Activity of *Coptidis Rhizoma* Extract

[Experiment Method]

In order to measure antitussive activity of *Coptidis Rhizoma* extracts of Examples 1-1 to 1-3, experiment was conducted using Tanaka et al. method (Motomu Tanaka and Kei Maruyama., J. Pharmacol. Sci. 93, 465~470, 2003., Daoui, Cognon, Naline et., Am. J. Respir. Crit. Care. Med. 158, 42~48, 1998) in the following procedure.

A test drug was orally administered to a male guinea pig (6-weeks age, Sam tako BioKorea), and after 1 hour, the guinea pig was put in a plethysmograph chamber (Buxco, U.S.A.), and then, a cough inducer, citric acid (Sigma) was nebulized to induce cough. As positive control, theobromine (Sigma) which is used as an antitussive was used. And, the guinea pig was exposed to 0.2M citric acid for 10 minutes, and the number of coughs occurred was measured for 15 minutes.

[Experiment Result]

The results are presented in the following Table 3.

TABLE 3

|  |  | dosage (mg/kg) | Capacity to suppress cough (%) |
|---|---|---|---|
| Example 1-1 | CR-GA | 200 | 33 |
|  | CR-GA-1 | 200 | 46 |
| Example 1-2 | CR-GB | 200 | 35 |
|  | CR-GB-1 | 200 | 52 |
| Example 1-3 | CR-GC | 200 | 44 |
| Positive control (Theobromine) |  | 50 | 57 |

As results of experiments, as shown in the above Table 3, the extracts had excellent activities as a whole, and particularly, CT-GB-1 of Example 1-2 showed most excellent cough suppression activity.

And, the activities of CR-GB-1 of Example 1-2 were measured according to dosage (50, 100, 150, 200 mg/kg), of which results are presented in the following Table 4.

TABLE 4

|  |  | dosage (mg/kg) | Capacity to suppress cough (%) |
|---|---|---|---|
| Example 1-2 | CR-GB-1 | 50 | 7 |
|  |  | 100 | 25 |
|  |  | 150 | 37 |
|  |  | 200 | 52 |
| Positive control (Theobromine) |  | 50 | 57 |

As results of experiment, as shown in the above Table 4, CR-GB-1 of Example 1-2 showed most excellent cough suppression activity at a dosage of 200 mg/kg.

3-3. Measurement of Antihistamine Activity of *Coptidis Rhizoma* Extract

[Experiment Method]

In order to measure antihistamine activity of *Coptidis Rhizoma* extract of Examples 1-1 to 1-3, experiment was conducted using Honuchi et al. method (Masako Honuchi and Yoshiyuki Seyama, J. Health Sci., 52(6), 711~717, 2006., Naoki Inagaki et al. Biol. Pharm. Bull. 24(7), 829~834, 2001.) in the following procedure.

Antihistamine effect was measured using peritoneal mast cell of a male rat (7-weeks age, Sam tako BioKorea) sensitized with ovalbumin. As positive control, Ketotifen (Sigma) was used. To a rat sensitized with ovalbumin, Ketotifen was orally administered at a concentration of 5 mg/kg, and test drugs were orally administered respectively at a concentration of 200 mg/kg for 4 days, and then, peritoneal mast cells were separated. The separated peritoneal mast cells ($2 \times 10^5$ cells/ml) were treated with Ketotifen at concentrations of 0.01 mg/ml, 0.1 mg/ml, and 1.0 mg/ml, and test drugs at concentrations of 0.1 mg/ml, 1.0 mg/ml, and 10 mg/ml. Finally, the mast cells were treated with compound 48/80 (Sigma) which activates non-immunological histamine release at a concentration of 10 µg/ml. At this time, the amount of histamine released from mast cells was quantified to examine whether the test materials suppress release of histamine from the mast cells. The relative amount of histamine released from mast cell in a rat to which no drug was administered was measured, of which results are presented in the following Table 5.

TABLE 5

| | | Oral dosage (mg/kg) | Concentration of mast cell treatment (mg/ml) | Histamine release amount (%) |
|---|---|---|---|---|
| Example 1-1 | CR-GA | 200 | 0 | 41 |
| | | | 0.1 | 38 |
| | | | 1.0 | 33 |
| | | | 10.0 | 26 |
| | CR-GA-1 | 200 | 0 | 44 |
| | | | 0.1 | 35 |
| | | | 1.0 | 29 |
| | | | 10.0 | 23 |
| Example 1-2 | CR-GB | 200 | 0 | 42 |
| | | | 0.1 | 38 |
| | | | 1.0 | 31 |
| | | | 10.0 | 27 |
| | CR-GB-1 | 200 | 0 | 39 |
| | | | 0.1 | 34 |
| | | | 1.0 | 27 |
| | | | 10.0 | 21 |
| Example 1-3 | CR-GC | 200 | 0 | 41 |
| | | | 0.1 | 37 |
| | | | 1.0 | 30 |
| | | | 10.0 | 22 |
| Positive control (Ketotifen) | | 5 | 0 | 43 |
| | | | 0.01 | 41 |
| | | | 0.1 | 32 |
| | | | 1.0 | 18 |

As results of experiments, as shown in the above Table 5, the extracts as a whole had excellent activities, and particularly, CR-GB-1 of Example 1-2 showed most excellent antihistamine activity.

And, the activities of CR-GB-1 of Example 1-2 were measured according to dosage (100, 200, 400 mg/kg), of which results are presented in the following Table 6.

TABLE 6

| | | Oral dosage (mg/kg) | Concentration of mast cell treatment (mg/ml) | Histamine release amount (%) |
|---|---|---|---|---|
| Example 1-2 | CR-GB-1 | 100 | 0 | 49 |
| | | | 0.1 | 40 |
| | | | 1.0 | 36 |
| | | | 10.0 | 30 |
| | | 200 | 0 | 42 |
| | | | 0.1 | 34 |
| | | | 1.0 | 27 |
| | | | 10.0 | 21 |
| | | 400 | 0 | 31 |
| | | | 0.1 | 26 |
| | | | 1.0 | 23 |
| | | | 10.0 | 18 |
| Positive control (Ketotifen) | | 5 | 0 | 43 |
| | | | 0.01 | 41 |
| | | | 0.1 | 32 |
| | | | 1.0 | 18 |

As results of experiments, as shown in the above Table 6, CR-GB-1 of Example 1-2 showed most excellent antihistamine activity at a dosage of 400 mg/kg.

3-4. Measurement of Antitussive Activities of Active Sub-Fractions

In order to measure antitussive activities of 5 sub-fractions prepared in the above Example 1-4, experiment for antitussive activity was conducted by the same method as Experiment 3-2, of which results are presented in the following Table 7.

TABLE 7

| | dosage (mg/kg) | Capacity to suppress cough (%) |
|---|---|---|
| Fr. 1 | 60 | 41 |
| Fr. 2 | 60 | 32 |
| Fr. 3 | 60 | 62 |
| Fr. 4 | 60 | 34 |
| Fr. 5 | 60 | 24 |
| Positive control Theobromine | 50 | 57 |

As results of experiment, as shown in Table 7, the fractions had excellent activities as a whole, and particularly, Fr. 3 showed most excellent antisussive activity.

3-5. Measurement of Antihistamine Activities of Active Sub-Fractions

In order to measure antihistamine activities of 5 sub-fractions prepared in the above Example 1-4, the same experiment was conducted as the above Experiment 3-3, of which results are presented in the following Table 8.

TABLE 8

| | Oral dosage (mg/kg) | Concentration of mast cell treatment (mg/ml) | Histamine release amount (%) |
|---|---|---|---|
| Fr. 1 | 60 | 0 | 55 |
| | | 0.1 | 50 |
| | | 1.0 | 42 |
| | | 10.0 | 39 |
| Fr. 2 | 60 | 0 | 59 |
| | | 0.1 | 54 |
| | | 1.0 | 48 |
| | | 10.0 | 41 |
| Fr. 3 | 60 | 0 | 38 |
| | | 0.1 | 31 |
| | | 1.0 | 26 |
| | | 10.0 | 19 |
| Fr. 4 | 60 | 0 | 56 |
| | | 0.1 | 50 |
| | | 1.0 | 44 |
| | | 10.0 | 40 |
| Fr. 5 | 60 | 0 | 66 |
| | | 0.1 | 62 |
| | | 1.0 | 55 |
| | | 10.0 | 51 |
| Positive control (Ketotifen) | 5 | 0 | 43 |
| | | 0.01 | 41 |
| | | 0.1 | 32 |
| | | 1.0 | 18 |

As results of experiment, as shown in the above Table 8, the fractions had excellent activities as a whole, and particularly, Fr. 3 showed most excellent antihistamine activity.

3-6. Analysis of Compounds of *Coptidis Rhizoma* Extract

In order to analyze the compounds of the *Coptidis Rhizoma* extracts and the fractions thereof of the above Examples, experiments were conducted using physicochemical analysis such as HPLC, LC/MS, UV-Spectrometer and FT-NMR.

As results, it was identified that berberine, palmatine, coptisine, columbamine and jatrorrhizine are contained in *Coptidis Rhizoma* extract. The contents of compounds of Coptidis extracts of Examples 1-1 to 1-4 were analyzed, of which results are presented in the following Table 9.

High performance liquid chromatography was measured using Waters Alliance 2695 model using Waters PDA 2996. As a column, YMC Hydrosphere C18, S-5 μm, 120 nm, 4.6×250 mm I.D, was used, and, sample temperature was maintained at 25° C.±1, and column temperature was maintained at 30° C.±1. A sample concentration was 1 mg/ml, injection amount was 10 μl, and flow rate was 1.0 ml/min. As standard materials, for berberine, palmatine and coptisine, those commercialized were purchased from Sigma Company and used, and for columbamine and jatrorrhizine, those purified from *Coptidis Rhizoma* were used. The mobile phase was gradient condition of 0.2% phosphoric acid solution (solvent A) and methanol (solvent B) of 0~60 minutes (A:B=9:1~6:4), 60~70 minutes (A:B=6:4~5:5), 70~90 minutes (A:B=5:5~0:10). The contents of the compounds in the extracts are indicated by area ratio for each standard material in weight percent.

TABLE 9

| | | Contents of compounds (%) | | | |
|---|---|---|---|---|---|
| | | Berberine | palmatine | coptisine | columbamine | jatrorrhizine |
| Example 1-1 | CR-GA | 15.6 | 4.2 | 4.3 | 0.6 | 0.6 |
| | CR-GA-1 | 25.3 | 4.5 | 4.7 | 0.6 | 0.5 |
| Example 1-2 | CR-GB | 22.8 | 5.6 | 6.5 | 1.5 | 0.9 |
| | CR-GB-1 | 27.0 | 7.1 | 5.2 | 0.9 | 0.8 |
| Example 1-3 | CR-GC | 30.9 | 7.8 | 6.2 | 1.1 | 1.0 |
| Example 1-4 | Fr. 1 | 0.5 | 0.2 | 0.1 | 0.1 | 0.1 |
| | Fr. 2 | 10.1 | 6.7 | 0.8 | 0.1 | 0.1 |
| | Fr. 3 | 47.0 | 21.4 | 3.7 | 3.2 | 1.5 |
| | Fr. 4 | 5.2 | 1.4 | 18.0 | 0.1 | 2.6 |
| | Fr. 5 | 0.1 or less | 0.1 or less | 0.1 or less | 0.1 or less | 0.1 or less |

As shown in the above Table 9, as results of comparing the contents of main compounds according to extracts and fractions, it was identified that 0.5 to 47.0 parts by weight of berberine, 0.2 to 21.4 parts by weight of palmatine, 0.1 to 18.0 parts by weight of coptisine, 0.1 to 3.2 parts by weight of columbamine, and 0.1 to 2.6 parts by weight of jatrorrhizine were contained.

3-7. Measurement of Expectorant Activity of Berberine

In order to measure expectorant activities of the *Coptidis Rhizoma* extracts of Examples 1-2 and 1-3, and 5 sub-fractions prepared in Example 1-4, the same experiment for expectorant activity as the above Experiment 1 was conducted, of which results are presented in the following Table 10, and a bar graph for the activities is shown in FIG. 1.

TABLE 10

| | dosage (mg/kg) | Capacity to discharge sputum (%) |
|---|---|---|
| Fr. 1 | 125 | 25 |
| Fr. 2 | 125 | 22 |
| Fr. 3 | 125 | 44 |
| Fr. 4 | 125 | 24 |
| Fr. 5 | 125 | 10 |
| CR-GB Example 1-2 | 125 | 32 |
| CR-GB-1 of Example 1-2 | 125 | 38 |
| CR-GC of Examle 1-3 | 125 | 37 |
| Berberine | 125 | 39 |
| Positive control Ambroxol | 250 | 34 |

Example 4

Figure 2:
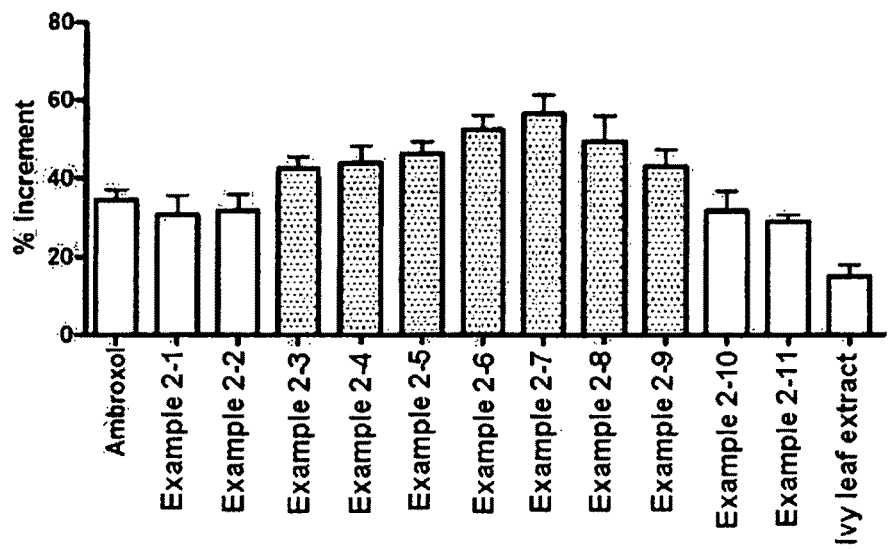
FIG. 2 shows expectorant activities of the extracts prepared in Example 2, indicating the results measured by phenol red method using a mouse.

Activity Test of Combined Extract of *Coptidis Rhizoma* with Ivy Leaf 4-1. Measurement of Expectorant Activity In order to evaluate expectorant activities of the combined extract and single extract prepared in the Example 2 (2-1 to 2-11), experiment was conducted by the same method as described in [Experiment method] of Experiment 3-1, using Engler, et al. method (Engler H, Szelenyi I, J. Pharmacol. Moth. 11, 151~157, 1984., Bao-quin Lin et., Pulmonary Pharmacology & Therapeutics 21, 259~263, 2008.), of which results are shown in FIG. 2. In FIG. 2, for positive control, Ambroxol was orally administered at a dosage of 250 mg/kg, and the rest test drugs were orally administered at a dosage of 500 mg/kg. And, for the extract of Example 2-7 showing most excellent activity, expectorant activities were measured according to dosage, of which results are presented in the following Table 11.

TABLE 11

| | dosage (mg/kg) | Capacity to discharge sputum (%) |
|---|---|---|
| Example 2-7 | 50 | 17 |
| | 100 | 30 |
| | 150 | 38 |
| | 200 | 44 |
| | 500 | 56 |
| Positive control | Ambroxol 250 | 34 |

As shown in FIG. 2, all the combined extracts of Examples 2-1 to 2-11 exhibited improved expectorant effects compared to ivy leaf extract alone, from which it can be identified that synergism for pharmacological activity occurs by combination of *Coptidis Rhizoma* extract and ivy leaf extract.

Particularly, Examples 2-3 to 2-9 exhibited more excellent expectorant effects than the existing expectorant Ambroxol, from which it is shown that if ivy leaf extract and *Coptidis Rhizoma* extract are combined at a weight ratio of 1:1 to 4:1, more increased expectorant effects can be obtained.

The above Table 11 shows the results of evaluations for the activities of Example 2-7 having highest activity according to dosage, and it is identified that the material of Example 2-7 has more excellent capacity to secrete sputum than positive control drug. Particularly, the material of Example 2-7 exhibits similar effect to positive control at a dosage of 100 mg/kg or more, and more excellent effect than positive control at a dosage of 150 mg/kg or more.

4-2. Measurement of Antitussive Activity

In order to measure antitussive activities of ivy leaf extract, and combined extract of *Coptidis Rhizoma* with ivy leaf (Examples 2-1 to 2-11) prepared in Example 2, experiment was conducted by the same method as described in [Experiment method] in the Experiment 3-2 using Tanaka et al. method (Motomu Tanaka and Kei Maruyama., J. Pharmacol. Sci. 93, 465~470, 2003., Daoui, Cognon, Naline et., Am. J. Respir. Crit. Care. Med. 158, 42~48, 1998.), of which results are shown in FIG. 3.

Figure 3:
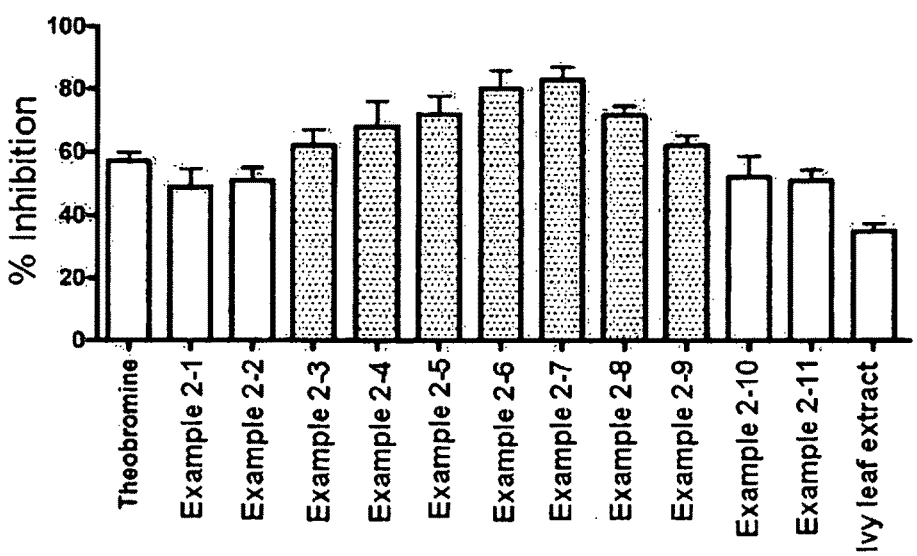
FIG. 3 shows antitussive activities of the extracts prepared in Example 2, indicating the results of cough suppression test using a guinea pig.

In FIG. 3, for positive control, Theobromine, was orally administered at a concentration of 50 mg/kg, and the rest test drugs were orally administered at a concentration of 200 mg/kg. And, for Example 2-7 showing most excellent activity, antitussive activities were evaluated according to dosage, of which results are presented in the following Table 12.

TABLE 12

| | dosage (mg/kg) | Capacity to suppress cough (%) |
|---|---|---|
| Example 2-7 | 50 | 29 |
| | 100 | 51 |
| | 150 | 69 |
| | 200 | 83 |
| Positive control Theobromine | 50 | 56 |

As shown in FIG. 3, all the combined extracts of Examples 2-1 to 2-11 exhibited increased antitussive effects than ivy leaf extract alone, from which it is identified that synergism for pharmacological activity occurs by combination of *Coptidis Rhizoma* extract with ivy leaf extract. Particularly, Examples 2-3 to 2-9 exhibited more excellent antitussive effects than the existing antitussive Theobromine, from which it is shown that if ivy leaf extract and *Coptidis Rhizoma* extract are combined at a weight ratio of 1:1 to 4:1, more excellent antitussive effects can be obtained.

And, the above Table 12 shows the results of evaluation for activities of Example 2-7 having highest activity according to dosage, from which it is shown that the material of Example 2-7 exhibits similar effect to positive control at a dosage of 100 mg/kg or more, and more excellent effect than positive control at a dosage of 150 mg/kg.

4-3. Measurement of Antihistamine Effect

In order to measure antihistamine effect of ivy leaf extract, and combined extract of *Coptidis Rhizoma* with ivy leaf (Examples 2-1 to 2-11) prepared in Example 2 in mast cell, experiment was conducted by the same method as described in [Experiment method] in Experiment 3-3 using Honuchi et al. method (Masako Honuchi and Yoshiyuki Seyama, J. Health Sci., 52(6), 711~717, 2006., Naoki Inagaki et. Biol. Pharm. Bull. 24(7), 829~834, 2001.), of which results are presented in the following Table 13. And, for Example 2-7 showing most excellent activity, antihistamine effects were measured according to dosage, and the results are presented in the following Table 14.

TABLE 13

| | Oral dosage (mg/kg) | Concentration of master cell treatment (mg/ml) | Histamine release amount (%) |
|---|---|---|---|
| Example 2-1 | 200 | 0 | 48 |
| | | 0.1 | 42 |
| | | 1.0 | 39 |
| | | 10.0 | 32 |
| Example 2-2 | 200 | 0 | 47 |
| | | 0.1 | 41 |
| | | 1.0 | 38 |
| | | 10.0 | 31 |
| Example 2-3 | 200 | 0 | 41 |
| | | 0.1 | 37 |
| | | 1.0 | 34 |
| | | 10.0 | 28 |
| Example 2-4 | 200 | 0 | 39 |
| | | 0.1 | 37 |
| | | 1.0 | 33 |
| | | 10.0 | 26 |
| Example 2-5 | 200 | 0 | 37 |
| | | 0.1 | 34 |
| | | 1.0 | 31 |
| | | 10.0 | 25 |
| Example 2-6 | 200 | 0 | 36 |
| | | 0.1 | 34 |
| | | 1.0 | 31 |
| | | 10.0 | 24 |
| Example 2-7 | 200 | 0 | 34 |
| | | 0.1 | 32 |
| | | 1.0 | 29 |
| | | 10.0 | 20 |
| Example 2-8 | 200 | 0 | 35 |
| | | 0.1 | 33 |
| | | 1.0 | 30 |
| | | 10.0 | 22 |
| Example 2-9 | 200 | 0 | 38 |
| | | 0.1 | 35 |
| | | 1.0 | 31 |
| | | 10.0 | 27 |
| Example 2-10 | 200 | 0 | 42 |
| | | 0.1 | 39 |
| | | 1.0 | 36 |
| | | 10.0 | 31 |
| Example 2-11 | 200 | 0 | 49 |
| | | 0.1 | 44 |
| | | 1.0 | 39 |
| | | 10.0 | 30 |
| Ivy leaf extract | 200 | 0 | 45 |
| | | 0.1 | 40 |
| | | 1.0 | 35 |
| | | 10.0 | 34 |
| Positive control | Ketotifen 5 | 0 | 44 |
| | | 0.01 | 41 |
| | | 0.1 | 32 |
| | | 1.0 | 19 |

TABLE 14

| | Oral dosage (mg/kg) | Concentration Of mast cell treatment (mg/ml) | Histamine release amount (%) |
|---|---|---|---|
| Example 2-7 | 100 | 0 | 49 |
| | | 0.1 | 39 |
| | | 1.0 | 35 |
| | | 10.0 | 34 |
| | 200 | 0 | 34 |
| | | 0.1 | 32 |
| | | 1.0 | 29 |
| | | 10.0 | 20 |
| | 400 | 0 | 21 |
| | | 0.1 | 18 |
| | | 1.0 | 17 |
| | | 10.0 | 17 |
| Ivy leaf extract | 200 | 0 | 45 |
| | | 0.1 | 40 |
| | | 1.0 | 35 |
| | | 10.0 | 34 |
| Positive control | Ketotifen 5 | 0 | 44 |
| | | 0.01 | 41 |
| | | 0.1 | 32 |
| | | 1.0 | 19 |

As shown in Table 13, it is identified that ivy leaf extract and the combined extracts of Examples 2-1 to 2-11 have antihistamine effect. Particularly, it is shown that if ivy leaf extract and *Coptidis Rhizoma* extract respectively exhibiting antihistamine activity are combined, synergism occurs. And, the above Table 14 shows the results of evaluation of Example 2-7 having most excellent activity according to dosage, and it is shown that the material of Example 2-7 exhibits excellent antihistamine activity.

4-4. Experiment for Suppression of Bronchoconstriction (In Vitro)

In order to measure bronchoconstrction suppression effects of the ivy leaf extract, and the combined extracts of *Coptidis Rhizoma* with ivy leaf (Examples 2-1 to 2-11) prepared in Example 2, experiment was conducted using Casoni G L et al. method (*Clin Exp Allergy.*, 33, 999-1004, 2003, *Anesth Analg.*, 89, 191-196, 1999, *Br J Pharmacol.*, 128, 577-584, 1999) in the following procedure.

Pentobarbital sodium (75/mg/kg) was intraperitoneally administered to male Hartely guinea pig (350~400 g, Daehan Biolink) to anesthetize it, and then, trachea was extracted. The extracted trachea was cut to about 3~5 mm in Krebs-Henseleit solution to divide into segments, and then, fixed in an organ bath and perfused with $10^{-4}$ M histamine to constrict the extracted trachea. And then, experiment material (0.50 mg/ml) was added thereto to measure change in the degree of tension of the extracted trachea. As a positive control drug, sodium nitroprusside dihydrate was used at a concentration of $2.6\times10^{-5}$ mg/ml. Supposing the constriction induced by $10^{-4}$ M histamine as 100%, relaxation rates (%) of experiment material administered groups and positive control drug administered group were calculated by subtracting the relaxation rate (%) of excipient control group from the relaxation rate (%) of experiment material administered group and positive control drug administered group obtained under the same conditions. The calculated bronchus relaxation rates (bronchoconstriction suppression activity) were shown in FIG. 4, and for Example 2-7 showing most excellent activity, trachea relaxation rates were measured according to dosage and the results are presented in the following Table 15.

TABLE 15

|  |  | concentration (mg/ml) | bronchus relaxation rate (%) |
|---|---|---|---|
| Example 2-7 |  | 0.25 | 20 |
|  |  | 0.50 | 48 |
|  |  | 1.00 | 83 |
| Positive control group | SNP | $2.6\times10^{-5}$ | 30 |

Figure 4:
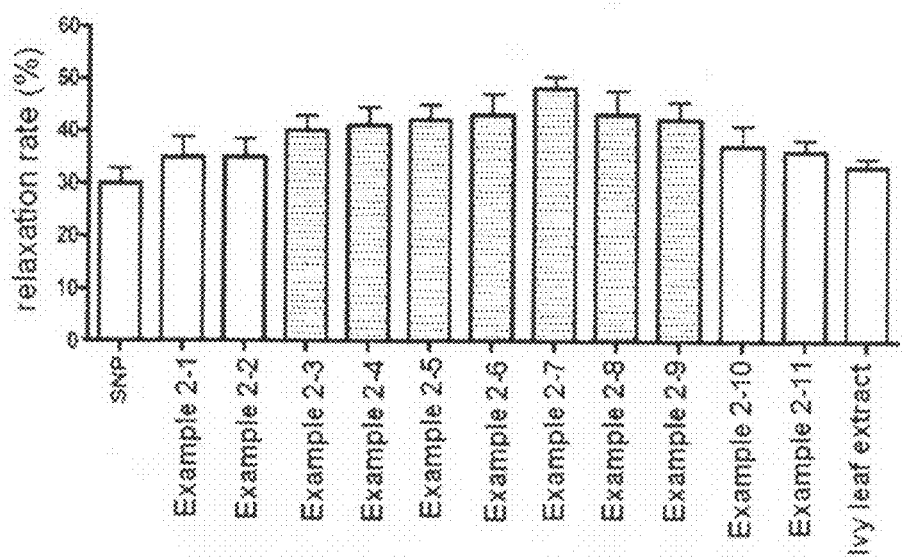
FIG. 4 shows bronchoconstriction suppression activities of the extracts prepared in Example 2, indicating relaxation (%) for a constriction inducer using a bronchus extracted from a guinea pig.

As shown in FIG. 4, it is identified that ivy leaf extract and the combined extracts of Examples 2-1 to 2-11 have bronchoconstriction suppression effect. And, it is shown that all the combined extracts of Examples 2-1 to 2-11 exhibit more increased suppression of bronchoconstriction than the extract of ivy leaf alone. The above Table 15 shows the results of evaluating the activities of Example 2-7 having most excellent activities according to dosage, from which it is shown that the material of Example 2-7 exhibits excellent suppression of bronchoconstriction.

4-5. Experiment for Anti-Asthma Effect Using a Murine Asthma Model

In order to confirm the anti-asthma effect using a murine asthma model of the combined extract of Example 2-7 which showed most excellent effects in the Experiments 4-1 to 4-4, experiment was conducted using Tang M. L. K. et al. method (Pulmonary Pharmacology & Therapeutics, 14, 203-210, 2001, Immunology and Cell Biology 79, 141-144, 2001, Journal of Experimental Medicine 189(10), 1621-1629, 1999). And, for evaluation, examination of airway hyper-responsiveness (AHR) for methacholine, examination of IgE value in blood plasma, examination of the number of cells and the distribution of white blood cells in bronchoalveolar lavage fluid (BALF), observation of pulmonary tissue, and RT-PCR (IL-1β, IL-4, IL-13r2a) were conducted.

[Experiment Method]

To a Balb/c mouse (18~21 g, Orientbio Inc.), an ovalbumin (OVA, Sigma) solution prepared for intraperitoneal injection was intraperitoneally administered in an amount of 500 ul (20 ug as OVA) per one mouse at Day 0 and Day 7, and it was sensitized with a solution prepared for OVA inhalation using a nubulizer (NE-U17, OMRON Co. Ltd, Japan) and then, the prepared 5% OVA solution was inhaled everyday for 30 minutes from Day 14 to Day 20. As positive control drug, 30 mg/kg of montelukast sodium was used, and all the experiment materials were used in an amount of 200 mg/kg. And, positive control drug and the experiment materials were orally administered everyday one hour before OVA inhalation for 7 days of from Day 14 to Day 20 after sensitization, and then, experiments were conducted by the following evaluation items.

1) Examination of Airway Hyper-Responsiveness (AHR) to Methacholine 24 hours after final inhalation of OVA (at Day 21), the mouse was put in a whole body plethysmograph (BUXCO, USA), each 0.4 ml of methacholine solutions of concentrations of 0, 10 and 20 mg/ml were taken to introduce in an aerosol, and inhaled to the mouse respectively for 3 minutes. And, Penh were measured for 4 minutes from the inhalation time, and the average value was set as Penh (enhanced pause) at corresponding dosage of methacholine.

2) Examination of IgE Value in Blood Plasma (Day 21)

For the animal measured according to 1), about 0.05 ml of blood was collected by orbital blood sampling and centrifuged, and the obtained plasma was divided into two parts and diluted to 1:10 to examine immunoglobulin E (IgE) value in plasma through IgE enzyme linked immunosorbent assay (ELISA; IgE ELISA kit for mouse, ME-151, SHIBAYAGI Co., Ltd., JAPAN).

3) Examination of the Number of Cells and the Distribution of White Blood Cells in Bronchoalveolar Lavage Fluid (BALF) (Day 22)

To the animals whose blood was sampled according to 2), sodium pentothal (50 mg/kg) was injected intraperitoneally to anesthetize it. And then, while fixing left lung with nippers, 0.4 ml of PBS solution was injected into bronchus and lung and then, extracted and its washed solution was taken, which was repeated three times. And, the solution was centrifuged at 1,500 g and supernatant was discarded, and then, 0.2 ml of PBS was added to the precipitate to suspend it again. For the suspension, the numbers of total leucocytes, neutrophils, eosinophils and lymphocytes were measured using automated hematology analyzers (Advia 120 coulter counter, BAYER, Germany).

4) Observation of Pulmonary Tissue

The left lung fixed with a nipper was taken off and fixed with a 10% formalin solution for one day, and then, paraffin-penetrated tissue using a tissue processor was cut to a thickness of 3-4 um using a microtome to make tissue fragments. The prepared slide was stained with eosin and the cover slide was covered with balsam, and observed with a microscope to examine the degree of occlusion of bronchiole and infiltration of inflammatory cells.

5) RT-PCR

Right pulmonary tissue was rapidly taken off and stored at −80° C. before experiment. RNA was separated from the tissue using RNA-Bee (Tel-Test Inc. USA), and the separated RNA was quantified at 260 nm using a spectrometer, and then, 4 ug of RNA and Oligo dT 2 ul (Promega), DEPC water were added to make 10 ul and the mixture was reacted at 65° C. for 5 minutes. And then, 5× reaction buffer 5 ul+RTase 2 ul+dNTP 5 ul+RNase inhibitor 1 ul+DEPC water 2 ul were introduced, and the total 25 ul of a mixture was reacted at 42° C. for 1 hour, and at 100° C. for 5 minutes to prepare cDNA. All the reagents used were purchased from Promega. PCR was conducted with prepared primers (IL-1β, IL-4, IL-13r2a). The primers used are as follow:

```
IL-1β forward:
5'-TCATGGGATGATGATGATAACCTGCT-3',    (Sequence No. 1)

IL-1β reverse:
5'-CCCATACTTTAGGAAGACACGGATT-3';     (Sequence No. 2)

IL-4 forward:
5'-TCATCGGCATTTTGAACGAG-3',          (Sequence No. 3)

IL-4 reverse:
5'-GAATCCAGGCATCGAAAAGC-3';          (Sequence No. 4)

IL-13r2a forward:
5'-GGTTATGCCAAATGCACTTGAG-3',        (Sequence No. 5)

IL-13r2a reverse:
5'-ATGGCTTTTTGTGCATATCAGAT-3'.       (Sequence No. 6)
```

PCR conditions are 32 cycle of 94° C. 30 seconds, 56° C. 30 seconds and 72° C. 1 minute. The PCR reactant was subjected to electrophoresis on a 2% agarose gel and dyed with EtBR, and then, UV was irradiated and density was compared and divided by actin density to analyze the value.

[Experiment Results]

1) Examination of Airway Hyper-Responsiveness (AHR) to Methacholine

Air hyper-responsivenesses to methacholine of montelukast (DR. REDDY'S) used as a positive control drug, ivy leaf extract, and the combined extracts of Examples 2-7 are presented in the following Table 16.

TABLE 16

| | Penh value according to methacholine dosage | | |
| --- | --- | --- | --- |
| | 0 mg/ml | 10 mg/ml | 20 mg/ml |
| Normal group | 1.2 ± 0.1 | 1.7 ± 0.2 | 6.0 ± 2.4 |
| Induced group | 1.5 ± 0.2 | 14.3 ± 3.0 | 29.7 ± 12.2 |
| Examples 2-7 (200 mg/kg) | 1.5 ± 0.2 | 7.5 ± 2.1 | 15 ± 4.9 |
| Ivy leaf extract (200 mg/kg) | 1.4 ± 0.2 | 8.2 ± 2.5 | 18.1 ± 5.9 |
| Positive control montelukast (30 mg/kg) | 1.5 ± 0.2 | 8.4 ± 2.4 | 19.8 ± 5.4 |

As shown in the above Table 16, the combined extracts of Examples 2-7 exhibit more excellent effect to suppress airway hyper-responsiveness than the extract of ivy leaf alone.

2) Examination of IgE Value in Plasma

IgE values in plasma of montelukast (DR. REDDY'S) used as a positive control drug, ivy leaf extract, and the combined extracts of Examples 2-7 according to concentrations are presented in the following Table 17.

TABLE 17

| | IgE level (ng/ml) |
| --- | --- |
| Normal group | 0.6 ± 0.2 |
| Induced group | 19.7 ± 6.1 |
| Examples 2-7 (200 mg/kg) | 9.6 ± 3.2 |
| Ivy leaf extract (200 mg/kg) | 11.0 ± 4.8 |
| Positive control montelukast (30 mg/kg) | 13.7 ± 5.7 |

As shown the above Table 17, the group receiving the materials of Examples 2-7 of the present invention has lower IgE value, which mediates inflammation, than the group receiving the extract of ivy leaf alone and the group receiving positive control drug.

3) The Number of Cells in Bronchoalveolar Lavage Fluid (BALF)

The numbers of neutrophils and eosinophils in bronchoalveolar lavage fluid (BALF) of montelukast (DR. REDDY'S) used as a positive control drug, ivy leaf extract, and the combined extracts of Examples 2-7 according to concentrations are presented in the following Table 18.

TABLE 18

| | WBC ($\times 10^3$ cells) | |
| --- | --- | --- |
| | NEU | EOS |
| Normal group | 16.3 ± 3.4 | 4.7 ± 2.7 |
| Induced group | 24.0 ± 6.1 | 414.7 ± 168.2 |
| Examples 2-7 (200 mg/kg) | 16.3 ± 11.3 | 296.7 ± 300.1 |
| Ivy leaf extract (200 mg/kg) | 18.7 ± 7.1 | 369.3 ± 232.2 |
| Positive control montelukast (30 mg/kg) | 22.3 ± 7.2 | 466.0 ± 207.0 |

NEU; neutrophil,
EOS; eosinophil

As shown in the above Table 18, the group receiving the materials of Examples 2-7 has lower count of white blood cells relating to inflammation (neutrophil, eosinophil) than the group receiving the extract of ivy leaf alone and the group receiving positive control drug.

4) Observation of Pulmonary Tissue

Figure 5:
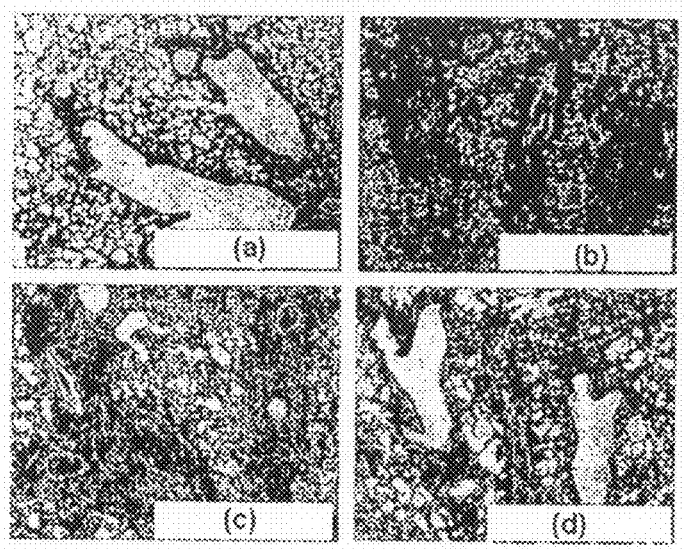
FIG. 5 shows the effects of the extracts of Examples 2~7 on bronchial occlusion in lung tissue, and inflammatory cell infiltration suppression activities in a pulmonary tissue of OVA-sensitized and tested mouse ((a) normal group, (b) induced group, (c) positive control, (d) examples 2~7).

The degrees of occlusion of bronchiole and infiltration of inflammatory cells of montelukast used as a positive control drug, ivy leaf extract, and the combined extracts of Examples 2-7 according to concentrations are presented in the following Table 19, and the photos of pulmonary tissue dyed by H & E staining are shown in FIG. 5. ((a) normal group, (b) induced group, (c) positive control group, (d) Examples 2-7). In the following Table 19, 1=No, 2=slight, 3=thin, 4=moderate, 5=thick according to the degrees of occlusion and infiltration of inflammatory cells.

TABLE 19

| | Microscope observation | |
| --- | --- | --- |
| | Degree of occlusion of bronchus | Degree of infiltration of inflammatory cells |
| Normal group | 0 ± 0 | 0 ± 0 |
| Induced group | 3.3 ± 0.5 | 3.8 ± 0.4 |
| Examples 2-7 (200 mg/kg) | 1.8 ± 0.4 | 1.9 ± 0.4 |
| Ivy leaf extract (200 mg/kg) | 2.0 ± 0.0 | 2.3 ± 0.5 |
| Positive control montelukast (30 mg/kg) | 3.5 ± 0.5 | 3.7 ± 0.5 |

As shown in the above Table 19, the combined extracts of Examples 2-7 exhibit more excellent effect to suppress occlusion of bronchus and infiltration of inflammatory cells than ivy leaf extract and positive control drug.

5) RT-PCR

The rates of expressing inflammation mediating cytokines (IL-1β, IL-4, IL-13r2a) of montelukast used as a positive control drug and the experiment materials of Examples 2-7 according to concentrations are presented in the following Table 20. In Table 20, each value is obtained by dividing the density of each cytokine according to UV irradiation by actin density.

TABLE 20

| | Degree of cytokine expression | | |
| --- | --- | --- | --- |
| | IL-1β | IL-4 | IL-13r2a |
| Normal group | 0.58 ± 0.27 | 0.58 ± 0.21 | 0.56 ± 0.49 |
| Induced group | 0.94 ± 0.39 | 1.96 ± 0.98 | 1.20 ± 0.67 |
| examples 2-7 (200 mg/kg) | 0.16 ± 0.74 | 0.83 ± 0.67 | 0.29 ± 0.96 |
| Ivy leaf extract (200 mg/kg) | 1.21 ± 0.62 | 0.14 ± 0.70 | 0.60 ± 0.70 |

TABLE 20-continued

| | | Degree of cytokine expression | | |
|---|---|---|---|---|
| | | IL-1β | IL-4 | IL-13r2a |
| Positive control | montelukast (30 mg/kg) | 0.51 ± 0.26 | 1.47 ± 0.48 | 0.37 ± 0.31 |

As shown in the above Table 20, in the group receiving the materials of Examples 2-7, expression of inflammation mediating cytokines (IL-1β, IL-4, IL-13r2a) is more suppressed compared to the group receiving the extract of ivy leaf alone and the group receiving positive control drug.

Example 5

Formulation of the Extract of *Coptidis Rhizoma*

5-1. Preparation of Powder

| | |
|---|---|
| the extract of Coptidis Rhizoma (Example 1-1) | 20 mg |
| lactose | 100 mg |
| talc | 10 mg |

The above ingredients were mixed and filled in a sealed sack to prepare a powder.

5-2. Preparation of Tablet

| | |
|---|---|
| the extract of Coptidis Rhizoma (Example 1-2) | 10 mg |
| cornstarch | 100 mg |
| lactose | 100 mg |
| magnesium stearate | 2 mg |

The above ingredients were mixed, and compressed by common tablet preparation method to prepare a tablet.

5-3. Preparation of Capsule

| | |
|---|---|
| the extract of Coptidis Rhizoma (Example 1-3) | 10 mg |
| crystalline cellulose | 3 mg |
| lactose | 14.8 mg |
| magnesium stearate | 0.2 mg |

The above ingredients were mixed by common capsule preparation method and filled in a gelatin capsule to prepare a capsule.

5-4. Preparation of Injection

| | |
|---|---|
| the extract of Coptidis Rhizoma (Example 1-4) | 10 mg |
| mannitol | 180 mg |
| sterile water for injection | 2974 mg |
| Na$_2$HPO$_4$,12H$_2$O | 26 mg |

One ample (2 ml) was prepared with the above contents of the ingredients by common injection preparation method.

5-5. Preparation of Solution

| | |
|---|---|
| the extract of Coptidis Rhizoma (Example 1-1) | 20 mg |
| high fructose corn syrup | 10 g |
| mannitol | 5 g |
| purified water | suitable amount |

According to common solution preparation method, each ingredient was added to purified water and dissolved therein, and lemon was added thereto in a suitable amount. And then, the above ingredients were mixed and purified water added thereto so that the total amount become 100 ml, and filled in a brown bottle and sterilized to prepare a solution.

5-6. Preparation of Health Food

| | |
|---|---|
| the extract of Coptidis Rhizoma (Example 1-2) | 1000 mg |
| vitamin A acetate | 70 μg |
| vitamin E | 1.0 mg |
| vitamin B1 | 0.13 mg |
| vitamin B2 | 0.15 mg |
| vitamin B6 | 0.5 mg |
| vitamin B12 | 0.2 μg |
| vitamin C | 10 mg |
| biotin | 10 μg |
| nicotinic acid amide | 1.7 mg |
| folic acid | 50 μg |
| calcium pantothenate | 0.5 mg |
| mineral mixture | suitable amount |
| ferrous sulfate | 1.75 mg |
| zinc oxide | 0.82 mg |
| magnesium carbonate | 25.3 mg |
| potassium phosphate monobasic | 15 mg |
| calcium phosphate dibasic | 55 mg |
| potassium citrate | 90 mg |
| calcium carbonate | 100 mg |
| magnesium chloride | 24.8 mg |

The above ratios of vitamins and mineral mixture illustrate a preferable example of mixing ingredients relatively suitable for health food; however, the ratios can be modified. And, the above ingredients can be mixed according to a common health food preparation method, and then, made into a granule, and used for preparation of a health food composition by common method.

5-7. Preparation of Health Beverage

| | |
|---|---|
| the extract of Coptidis Rhizoma (Example 1-3) | 1000 mg |
| Citric acid | 1000 mg |
| oligosaccharide | 100 g |
| Japanese apricot concentrate | 2 g |
| taurin | 1 g |
| purified water | dded so as to reach a total amount of 900 ml |

The above ingredients were mixed according to a common health beverage preparation method, and heated with agitation at 85° C. for about 1 hour, and then, the prepared solution was filtered to collect in a sterilized 2 l vessel, seal sterilized and refrigeration stored.

The above ratios illustrate a preferable example of mixing ingredients relatively suitable for a favorite beverage; however, it can be modified according to regional and ethnic taste such as a demand class, a demand country, use, etc.

Example 6

Formulation of Combined Extract of *Coptidis Rhizoma* with Ivy Leaf 6-1. Preparation of Tablet 200 mg of the combined extract of Example 2-7, 10 mg of light anhydrous silicic acid, 2 mg of magnesium stearate, 50 mg of microcrystalline cellulose, 25 mg of starch sodium glycolic acid, 113 mg of cornstarch and suitable amount of anhydrous ethanol were mixed and compressed to a tablet by a common method.

6-2. Preparation of Health Food

| | |
|---|---|
| combined extract (example 2-7) | 1000 mg |
| vitamin A acetate | 70 μg |
| vitamin E | 1.0 mg |
| vitamin B1 | 0.13 mg |
| vitamin B2 | 0.15 mg |
| vitamin B6 | 0.5 mg |
| vitamin B12 | 0.2 μg |
| vitamin C | 10 mg |
| biotin | 10 μg |
| nicotinic acid amide | 1.7 mg |
| folic acid | 50 μg |
| calcium pantothenate | 0.5 mg |
| mineral mixture | suitable amount |
| ferrous sulfate | 1.75 mg |
| zinc oxide | 0.82 mg |
| magnesium carbonate | 25.3 mg |
| potassium phosphate monobasic | 15 mg |
| calcium phosphate dibasic | 55 mg |
| potassium citrate | 90 mg |
| calcium carbonate | 100 mg |
| magnesium chloride | 24.8 mg |

The above ratios of vitamin and mineral mixture illustrate a preferable example of mixing ingredients relatively suitable for a health food; however, the ratios can be modified. And, the above ingredients can be mixed by a common health food preparation method, made into a granule, and used for preparation of health food by common method.

6-3. Preparation of Health Beverage

| | |
|---|---|
| combined extract (Example 2-7) | 1000 mg |
| citric acid | 1000 mg |
| oligosaccharide | 100 g |
| Japanese apricot concentrate | 2 g |
| taurin | 1 g |
| purified water | added so as to reach a total amount of 900 ml |

The above ingredients were mixed by a common health beverage preparation method, and then, heated with agitation at 85° C. for about 1 hour, and then, the obtained solution was filtered and introduced in a sterilized 2 l vessel, and seal sterilized and then refrigeration stored.

The above ratios illustrate a preferable example of mixing ingredients relatively suitable for a health beverage; however, the ratios can be modified according to regional and ethnic taste such as a demand class, a demand country, use, etc.

---

The invention claimed is:

1. A method of treating respiratory disease comprising the step of administering a composition consisting essentially of a combination of a *Coptidis rhizoma* extract and a ivy leaf extract as an active ingredient,
   wherein the weight ratio of the ivy leaf extract and the *Coptidis rhizoma* extract is 0.1:1 to 10:1 (the weight of the ivy leaf extract: the weight of the *Coptidis rhizoma* extract),
   wherein the respiratory disease is selected from the group consisting of pulmonary emphysema, bronchitis, asthma, chronic or acute bronchoconstriction, stridulus infant syndrome, chronic obstructive pulmonary disease, bronchial adenoma, solitary pulmonary nodule, pulmonary tuberculosis, pyothorax, pulmonary abscess, common cold, influenza, and pulmonary histiocytosis.

2. The method according to claim 1, wherein the weight ratio of the ivy leaf extract and the *Coptidis rhizoma* extract is 0.2:1 to 5:1 (the weight of ivy leaf extract: the weight of the *Coptidis rhizoma* extract).

3. The method according to claim 1, wherein the dosage of the composition per day is 0.5 to 500 mg/kg, based on the amount of the active ingredient.

* * * * *

SEQUENCE LISTING

<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: IL-1beta forward primer

<400> SEQUENCE: 1
tcatgggatg atgatgataa cctgct                                          26

<210> SEQ ID NO 2
<211> LENGTH: 25
<212> TYPE: DNA
<213> ORGANISM: Artificial Sequence
<220> FEATURE:
<223> OTHER INFORMATION: IL-1beta reverse primer

<400> SEQUENCE: 2
cccatacttt aggaagacac ggatt                                           25

<210> SEQ ID NO 3
<211> LENGTH: 20
<212> TYPE: DNA
<213> ORGANISM: Artificial Sequence
<220> FEATURE:
<223> OTHER INFORMATION: IL-4 forward primer

<400> SEQUENCE: 3
tcatcggcat tttgaacgag                                                 20

```
<210> SEQ ID NO 4
<211> LENGTH: 20
<212> TYPE: DNA
<213> ORGANISM: Artificial Sequence
<220> FEATURE:
<223> OTHER INFORMATION: IL-4 reverse primer

<400> SEQUENCE: 4
gaatccaggc atcgaaaagc                                                   20

<210> SEQ ID NO 5
<211> LENGTH: 22
<212> TYPE: DNA
<213> ORGANISM: Artificial Sequence
<220> FEATURE:
<223> OTHER INFORMATION: IL-13r2a forward primer

<400> SEQUENCE: 5
ggttatgcca aatgcacttg ag                                                22

<210> SEQ ID NO 6
<211> LENGTH: 23
<212> TYPE: DNA
<213> ORGANISM: Artificial Sequence
<220> FEATURE:
<223> OTHER INFORMATION: IL-13r2a reverse primer

<400> SEQUENCE: 6
atggcttttt gtgcatatca gat                                               23
```